US009762001B2

United States Patent
Morello et al.

(10) Patent No.: US 9,762,001 B2
(45) Date of Patent: Sep. 12, 2017

(54) RIGHT ANGLED COAXIAL ELECTRICAL CONNECTOR AND METHODS FOR VERIFYING PROPER ASSEMBLY THEREOF

(71) Applicant: Delphi Technologies, Inc., Troy, MI (US)

(72) Inventors: John R. Morello, Warren, OH (US); James M. Rainey, Warren, OH (US)

(73) Assignee: DELPHI TECHNOLOGIES, INC., Troy, MI (US)

( * ) Notice: Subject to any disclaimer, the term of this patent is extended or adjusted under 35 U.S.C. 154(b) by 0 days.

(21) Appl. No.: 15/011,957

(22) Filed: Feb. 1, 2016

(65) Prior Publication Data

US 2017/0222368 A1    Aug. 3, 2017

(51) Int. Cl.
| H01R 13/627 | (2006.01) |
| H01R 13/641 | (2006.01) |
| H01R 24/40 | (2011.01) |
| G01N 21/95 | (2006.01) |
| G01R 31/02 | (2006.01) |

(52) U.S. Cl.
CPC ......... H01R 13/641 (2013.01); G01N 21/95 (2013.01); G01R 31/026 (2013.01); H01R 24/40 (2013.01)

(58) Field of Classification Search
CPC ............................ H01R 13/641; H01R 24/40
USPC .................................................. 439/578, 354
See application file for complete search history.

(56) References Cited

U.S. PATENT DOCUMENTS

| 5,061,206 A | 10/1991 | Kawanami et al. |
| 6,036,540 A | 3/2000 | Beloritsky |
| 6,116,945 A * | 9/2000 | Davis ................. H01R 13/5825 439/354 |
| 6,305,947 B1 | 10/2001 | Bruce |
| 6,361,348 B1 | 3/2002 | Hall et al. |
| 6,676,445 B2 | 1/2004 | Hall et al. |
| 6,860,761 B2 * | 3/2005 | Lee ........................ H01R 4/28 439/582 |
| 7,021,966 B2 | 4/2006 | Ikeda et al. |
| 7,070,440 B1 | 7/2006 | Zerebilov et al. |
| 7,207,839 B1 * | 4/2007 | Shelly .................. H01R 4/2404 439/585 |

(Continued)

FOREIGN PATENT DOCUMENTS

JP    4888563 B2    2/2012

*Primary Examiner* — Abdullah Riyami
*Assistant Examiner* — Nader Alhawamdeh
(74) *Attorney, Agent, or Firm* — Robert J. Myers

(57) ABSTRACT

A right angled coaxial electrical connector is provided and includes a housing having a first and second opening and a first terminal disposed within the internal cavity that is configured to be connected to a center conductor of a coaxial cable inserted in the first opening. The connector also includes a center contact disposed within the internal cavity, accessible through the second opening, and defining a corresponding second terminal configured to receive a tip of the first terminal. The connector additionally includes a conductive shield surrounding the center contact and disposed within the internal cavity and an insulator intermediate the shield and the center contact. The insulator defines a portal extending from the second opening to the location of the tip of the first terminal when fully seated within the second terminal. Methods of verifying proper assembly of the right angled coaxial electrical connector are also provided.

8 Claims, 10 Drawing Sheets

(56) References Cited

U.S. PATENT DOCUMENTS

| | | |
|---|---|---|
| 8,251,762 B2 | 8/2012 | Maier et al. |
| 8,628,352 B2 * | 1/2014 | Nugent .................... H01R 9/05 439/578 |
| 9,214,771 B2 | 12/2015 | Nugent |
| 2003/0082950 A1 * | 5/2003 | Tang .................... H01R 9/0524 439/582 |
| 2004/0137790 A1 | 7/2004 | Lee et al. |
| 2008/0293298 A1 | 11/2008 | Burris et al. |
| 2011/0230092 A1 * | 9/2011 | Maier .................... H01R 13/64 439/578 |
| 2012/0252267 A1 * | 10/2012 | Nugent ................ H01R 24/545 439/582 |
| 2013/0012062 A1 * | 1/2013 | Nugent .................... H01R 9/05 439/578 |

* cited by examiner

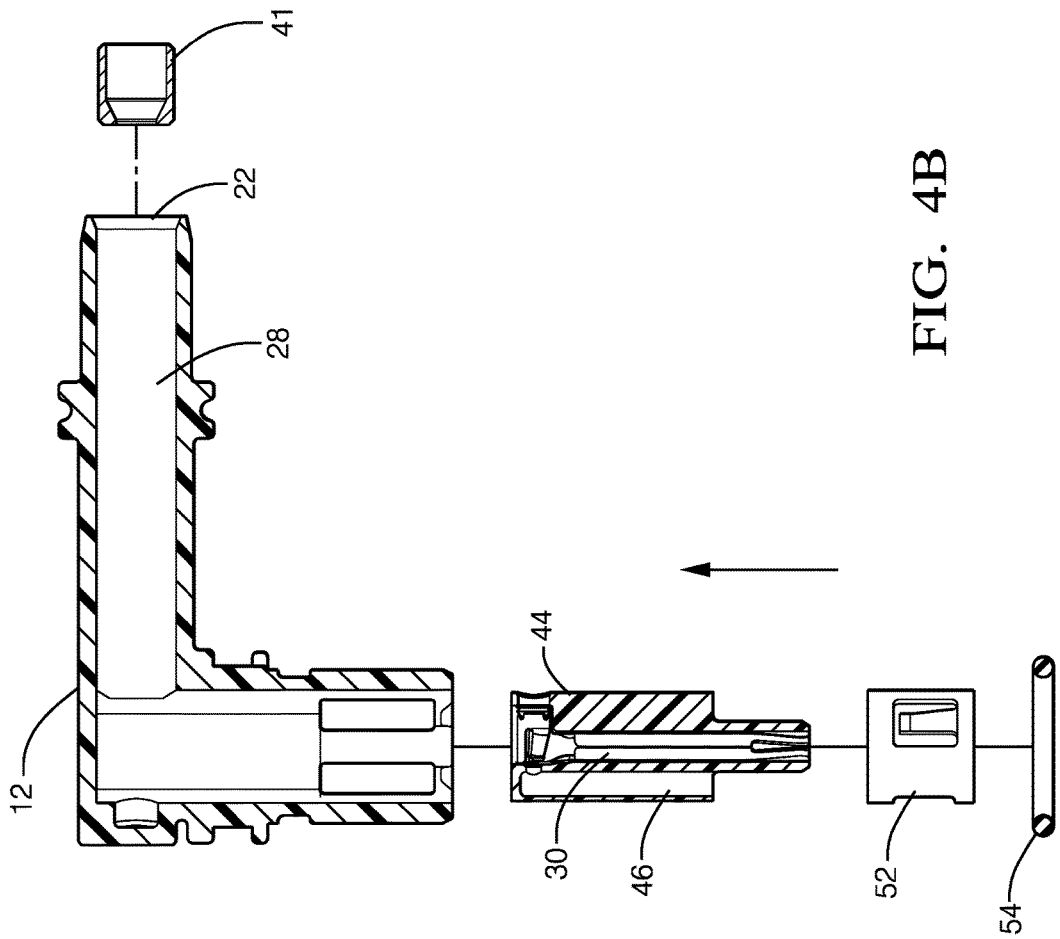
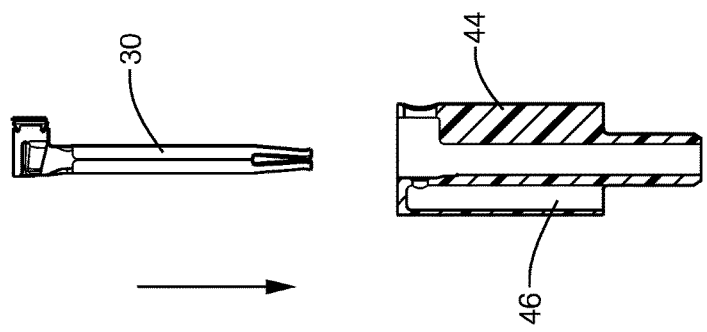
FIG. 4B
FIG. 4A

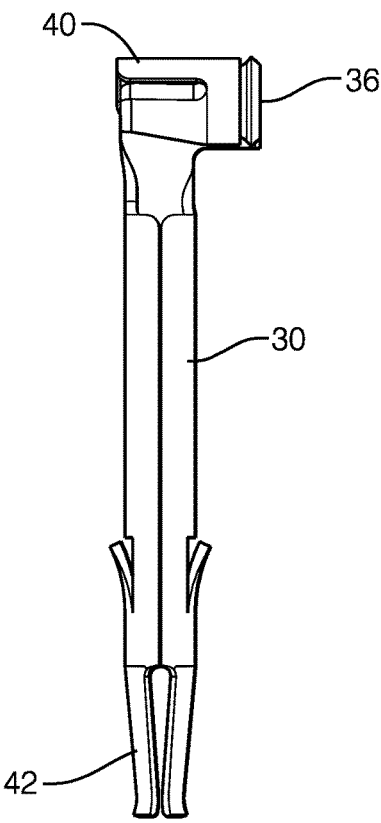
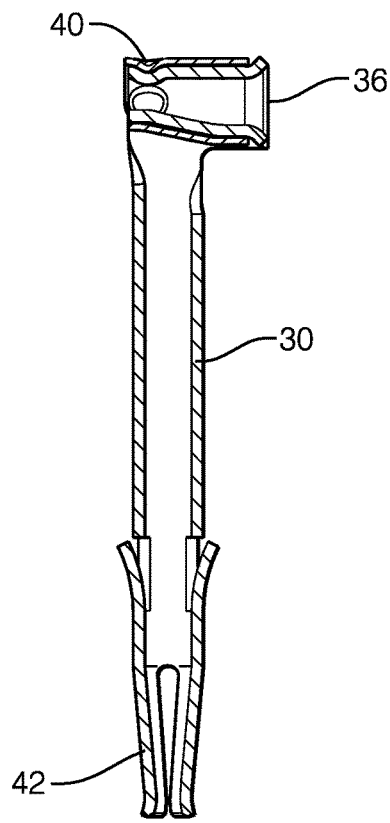
FIG. 5A    FIG. 5B
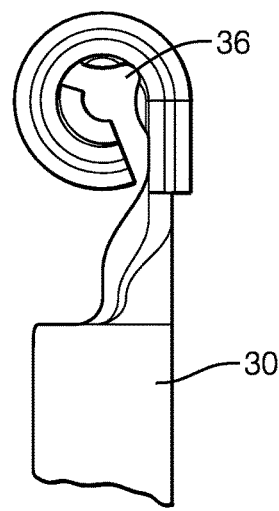
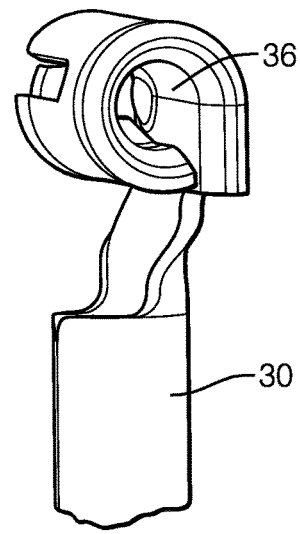
FIG. 5C    FIG. 5D

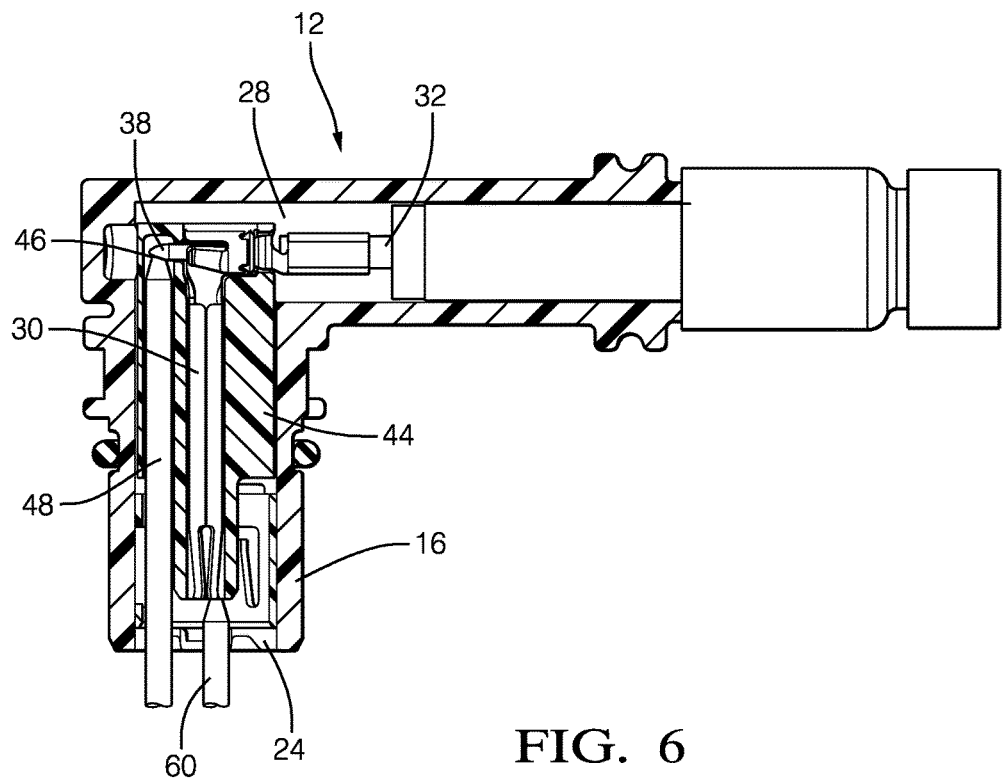
FIG. 6
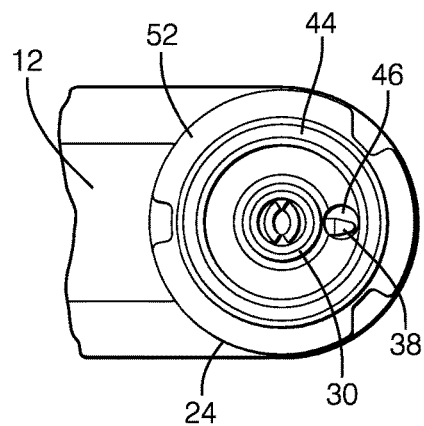
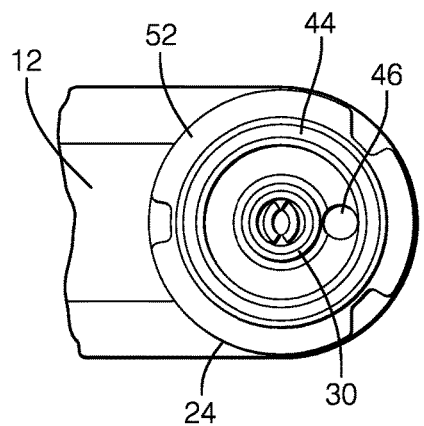
FIG. 7A　　　　FIG. 7B

RIGHT ANGLED COAXIAL ELECTRICAL CONNECTOR AND METHODS FOR VERIFYING PROPER ASSEMBLY THEREOF

TECHNICAL FIELD OF THE INVENTION

The present invention relates generally to electrical connectors and, more particularly, to a right angled coaxial electrical connector.

BACKGROUND OF THE INVENTION

Radio frequency (RF) coaxial cable connector assemblies have been used for numerous automotive applications, such as global positioning systems (GPS), infotainment systems, and air bag systems. Coaxial cables typically consist of an outer shield conductor, an inner center conductor, a dielectric, and an insulation jacket. The outer conductor and the inner conductor of the cable often electrically interface with a mating coaxial cable through socket and plug connectors. Such conventional coaxial cable connectors are known in the art.

In order to standardize various types of connectors and thereby avoid confusion, certain industry standards have been established. One of these standards is referred to as FAKRA. FAKRA is the Automotive Standards Committee in the German Institute for Standardization (in German "Deutsches Institut für Normung", best known by the acronym DIN), representing international standardization interests in the automotive field. The FAKRA standard provides a system, based on keying and color coding, for proper connector attachment. Like socket keys can only be connected to like plug keyways in FAKRA connectors. Secure positioning and locking of connector housings is facilitated by way of a FAKRA defined catch on the socket housing and a cooperating latch on the plug housing.

Certain automotive applications may require that coaxial cables be installed with a 90 degree bend at the end of the cable, for example in the case of a cable that terminates at the rear of a dashboard. Usually, the central conductor of the coaxial cable is connected perpendicularly with the central contact of the right angle coaxial connector within an interior chamber provided proximate to the 90 degree bend in the coaxial connector. The connection is established by a terminal connected to the center conductor of the cable being received by a corresponding terminal of the center after the coaxial cable is inserted through a cable opening in the connector housing so that the central conductor is positioned in the interior chamber. Access to the interior chamber from the exterior of the connector is afforded through an access opening, which is sealed by a removable closure. The terminal on the center conductor is inserted into the corresponding terminal of the center conductor with the closure removed so that proper connection of the terminals may be verified. Subsequently, the removable closure is replaced over the access opening to seal the interior chamber against signal leakage and to prevent inward penetration of contaminants from the environment surrounding the right angle coaxial connector.

Conventional right angle coaxial connectors suffer from several deficiencies and shortcomings. For example, conventional right angle coaxial connectors are difficult to produce due to need to provide an interior chamber accessible through an access opening covered by a removable closure. Visual inspection of the terminals may be difficult. In addition, the presence of the removable closure increases manufacturing costs of the connector and the effort required to accomplish the solder connection. Moreover, the removable closure may be misplaced or lost when the right angle coaxial connector is assembled with the coaxial cable.

Therefore, it would be desirable to have a right angle coaxial connector that simplifies verification of a connection between the central conductor of a coaxial cable and the central pin of a coaxial connector.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

BRIEF SUMMARY OF THE INVENTION

In accordance with an embodiment of the invention, a right angled coaxial electrical connector is provided. The right angled coaxial electrical connector includes a housing having a first opening and a second opening. The first opening is oriented at substantially a ninety degree angle to the second opening. The housing defines an internal cavity extending from the first opening to the second opening. The connector further includes a first terminal disposed within the internal cavity and configured to be connected to a center conductor of a coaxial cable inserted in the first opening. The connector also includes a center contact disposed within the internal cavity. The center contact is accessible through the second opening. The center contact defines a corresponding second terminal configured to receive a tip of the first terminal therethrough. The connector additionally includes a conductive shield surrounding the center contact that is disposed within the internal cavity and an insulator intermediate the shield and the center contact. The insulator defines a portal extending from the second opening to the location of the tip of the first terminal when fully seated within the second terminal. The housing does not have a third opening to the internal cavity and did not have a third opening to the internal cavity that is now enclosed by a cover.

In accordance with another embodiment of the invention, a method verifying proper assembly of a right angled coaxial electrical connector is provided. The method includes providing a right angled coaxial electrical connector substantially as described above. The method also includes the steps of inserting a first conducive probe within the portal to the location of the tip of the first terminal when fully seated within the second terminal, contacting the center contact with a second conductive probe, and checking for electrical continuity between the first probe and the second probe.

In accordance with yet another embodiment of the invention, an alternative method verifying proper assembly of a right angled coaxial electrical connector is provided. The method includes providing a right angled coaxial electrical connector substantially as described above. The method also includes the step of visually inspecting the portal to verify that the tip of the first terminal is at the location when fully seated within the second terminal. The step of visually inspecting the portal may be performed by a machine vision system.

BRIEF DESCRIPTION OF THE SEVERAL VIEWS OF THE DRAWING

The present invention will now be described, by way of example with reference to the accompanying drawings, in which:

FIG. 4A is an exploded cut away view of the center contact and insulator of the right angle coaxial connector of FIG. 2 according to one embodiment;

FIG. 4B is an exploded cut away view of the right angle coaxial connector of FIG. 2 according to one embodiment;

FIG. 5A is a side view of the center contact of the right angled coaxial connector of FIG. 1A according to one embodiment;

FIG. 5B is a cut away view of the center contact of FIG. 5A according to one embodiment;

FIG. 5C is a close up end view of a top terminal of the center contact of FIG. 5A according to one embodiment;

FIG. 5D is a perspective view of the top terminal of the center contact of FIG. 5C according to one embodiment;

FIG. 6 is a cut away side view of the right angle coaxial connector of FIG. 2 with the coaxial cable of FIG. 1A properly connected to the center contact and electrical probes used to verify the proper connection according to one embodiment;

FIG. 7A is an end view of the right angle coaxial connector of FIG. 1A with the coaxial cable of FIG. 4 properly connected to the center contact and visible through the portal in the insulator surrounding the center contact according to one embodiment;

FIG. 7B is an end view of the right angle coaxial connector of FIG. 1A with the coaxial cable of FIG. 4 improperly connected to the center contact and not visible through the portal in the insulator surrounding the center contact according to one embodiment;

DETAILED DESCRIPTION OF THE INVENTION

Presented herein is a description of a right angled coaxial connector configured for terminating a coaxial cable. The connector is designed to allow easy verification of a connection between the center conductor of the coaxial cable and the center contact of the right angled connector. An insulator surrounding the center contact includes a portal running to the location of the connection between the center conductor of the coaxial cable and the center contact. This portal allows verification of proper connection between the center conductor and the center contact using electrical contact or visual inspection techniques.

Figure 1:
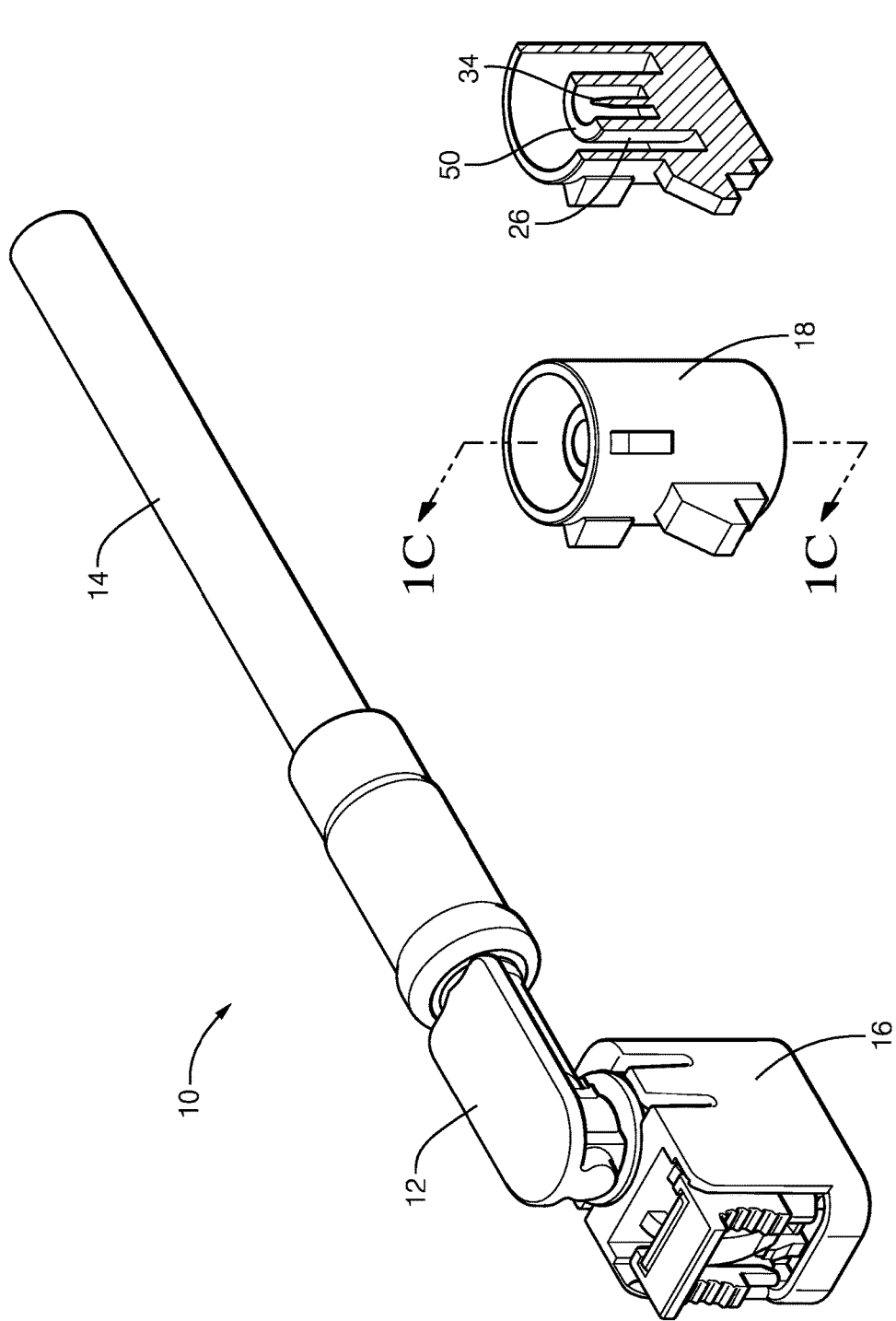
FIG. 1A is a perspective view of a coaxial cable assembly according to one embodiment.
FIG. 1B is a perspective view of a mating connector for the coaxial cable assembly of FIG. 1A according to one embodiment.
FIG. 1C is a cross sectional perspective view of the mating of FIG. 1B according to one embodiment

FIG. 1A illustrates a non-limiting example of a coaxial cable assembly 10. The assembly 10 includes a right angled coaxial electrical connector 12, hereinafter referred to as the connector 12, a coaxial cable 14, and an outer housing 16 having a keyed locking mechanism surrounding the connector 12. The connector 12 is configured to interconnect with a corresponding mating connector 18 shown in FIG. 1B. The assembly's 10 outer housing 16 is color coded to match the mating connector 18 and configured to receive the key tabs and lock with the locking tab of the mating connector 18.

Figure 2:
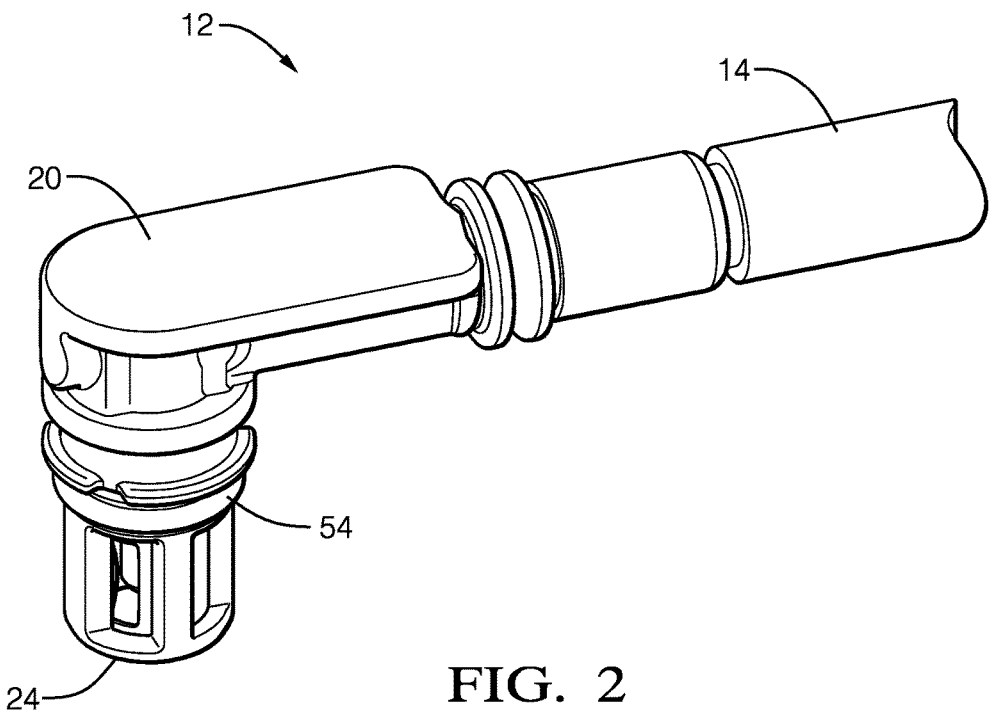
FIG. 2 is a perspective view of a right angled coaxial connector of the coaxial cable assembly of FIG. 1A according to one embodiment.
Figure 3:
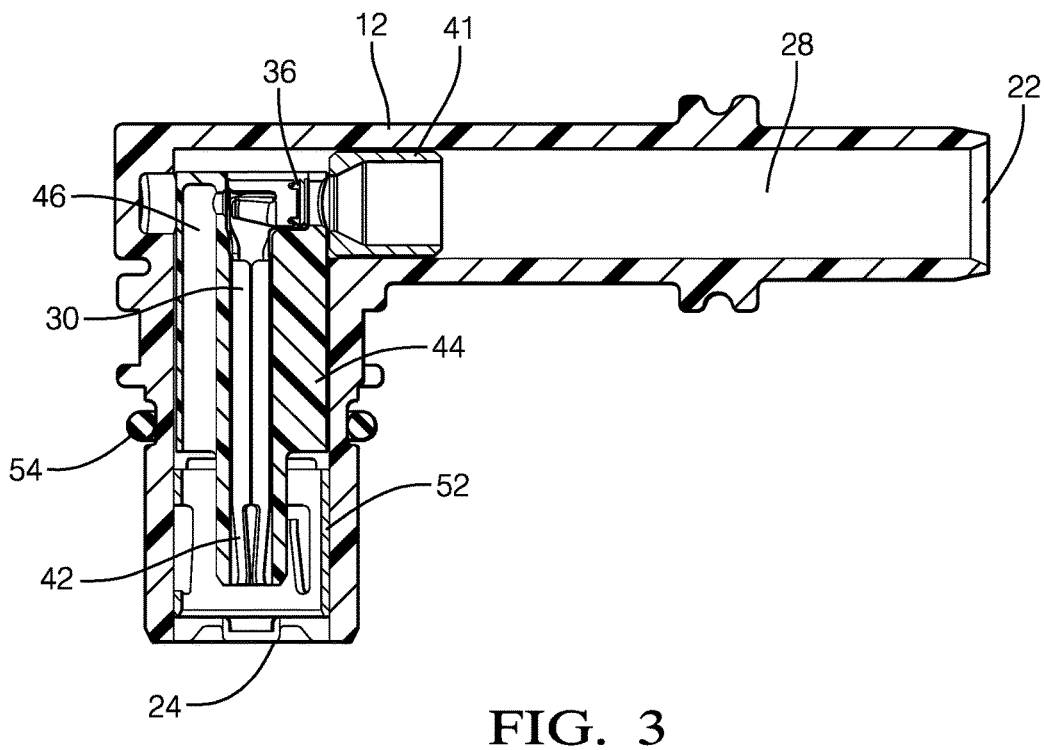
FIG. 3 is a cut-away side view of the right angled coaxial connector of FIG. 2 according to one embodiment.

As shown in FIGS. 2 and 3, the connector 12 includes an inner housing 20 having a first opening 22 and a second opening 24. The first opening 22 is oriented at substantially a 90° angle to the second opening 24. As used herein, substantially right angled means±10° of 90°. The inner housing 20 is formed of an electrically conductive material to provide electrical continuity between an outer shield conductor of the coaxial cable 14 and a shield connector 26 of the mating connector 18 and to provide electromagnetic shielding of electrical signals flowing through the connector 12.

As shown in FIGS. 3 and 4B, the inner housing 20 defines an internal cavity 28 that extends from the first opening 22 to the second opening 24. The first opening 22 is configured to receive the coaxial cable 14 as shown in FIG. 1A while the second opening 24 is configured to receive the mating connector 18. The internal cavity 28 also has a substantially 90° angled bend. The inner housing 20 is integrally formed by a casting or machining process. The inner housing 20 does not have any other openings other than the first and second openings. The inner housing 20 does not include any other openings nor did the inner housing 20 include any other opening that is now covered. This allows the internal cavity 28 to be more easily sealed from external contaminants that may enter the cavity.

As illustrated in FIG. 3, the connector 12 further includes a center contact 30 disposed within the internal cavity 28 that is configured to interconnect the center conductor 32 of the coaxial cable 14 with a corresponding mating center contact 34 in the mating connector 18. As shown in FIGS. 3 and 5A-5D, the top end of the center contact 30 defines a first female socket terminal 36 that is configured to receive a male plug terminal 38 attached to the center conductor 32 of the coaxial cable 14 (see FIG. 6). The first socket terminal 36 is surrounded by a compression spring 40 to increase the contact force between the first socket terminal 36 and the plug terminal 38. The first socket terminal 36 is accessible through the first opening 22 of the inner housing 20. The connector 12 also includes a tapered ferrule 41 disposed within the first opening 22 that is configured to guide the plug terminal 38 into the first socket terminal 36. As shown in FIG. 6, when plug terminal 38 is fully seated in the first socket terminal 36, the plug terminal 38 protrudes from both sides of the first socket terminal 36. Other embodiments may omit a plug terminal and in these embodiments, the center conductor 32 is inserted directly into the first socket terminal 36.

The bottom end of the center contact 30 defines a second socket terminal 42 that is accessible through the second opening 24 and is configured to receive a mating plug terminal (not shown) of the corresponding mating center contact 34 in the mating connector 18.

An insulator 44 surrounds the center contact 30 and is located intermediate the center contact 30 and the walls of the internal cavity 28. The insulator 44 defines a portal 46 that extends generally parallel to the center contact 30 from the second opening 24 to the location of the plug terminal 38 when it is fully seated within the first socket terminal 36. This portal 46 may be used to insert a conductive probe 48 to contact the tip of the plug terminal 38 as shown in FIG. 6. The portal 46 may be alternatively used to visually inspect for the tip of the plug terminal 38 as shown in FIGS. 7A and 7B. The insulator 44 defines a neck configured to be inserted into a corresponding feature in a mating insulator 50 in the mating connector 18.

The connector 12 additionally includes a conductive shield spring 52 surrounding the neck of the insulator 44 and in contact with the inner housing 20. The shield spring 52 defines spring fingers to increase contact force between the inner housing 20 and the corresponding shield of the mating connector 18.

The connector 12 also includes a compliant seal 54 contained in a circumferential groove running parallel to the second opening 24. This seal 54 is configured to inhibit the intrusion of environmental contaminants in to the internal cavity 28 or the junction between the connector 12 and the mating connector 18.

Figure 8:
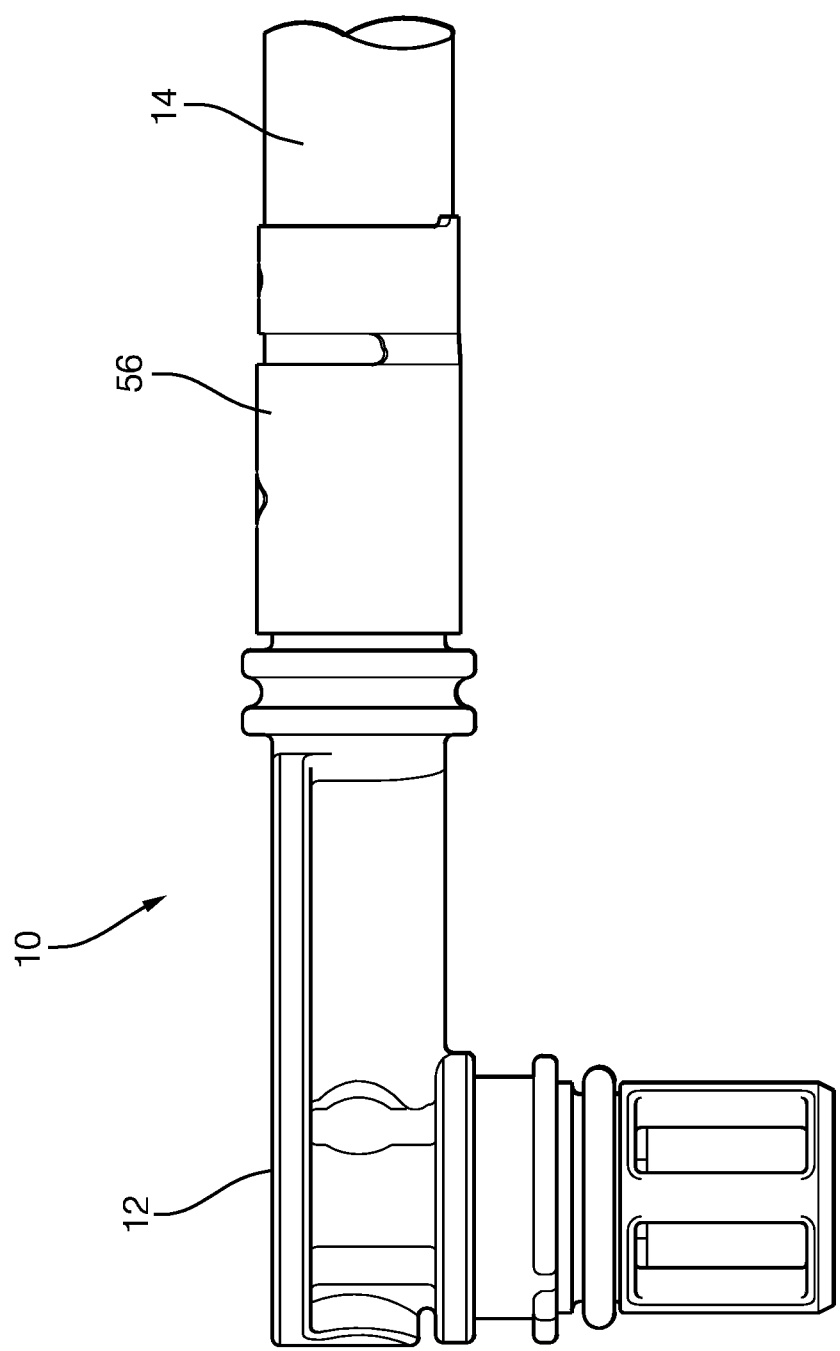
FIG. 8 is a side view the right angle coaxial terminal of FIG. 2 crimped to the coaxial cable of FIG. 2 by a ferrule according to one embodiment.

As shown in FIG. 8, the assembly 10 includes a crimping ferrule 56 over the junction between the shield conductor of the coaxial cable 14 and the connector 12 in order to improve mechanical retention for the connector 12 to the coaxial cable 14 and improve the electrical connection between the coaxial cable's shield conductor and the inner housing 20 of the connector 12.

Figure 9:
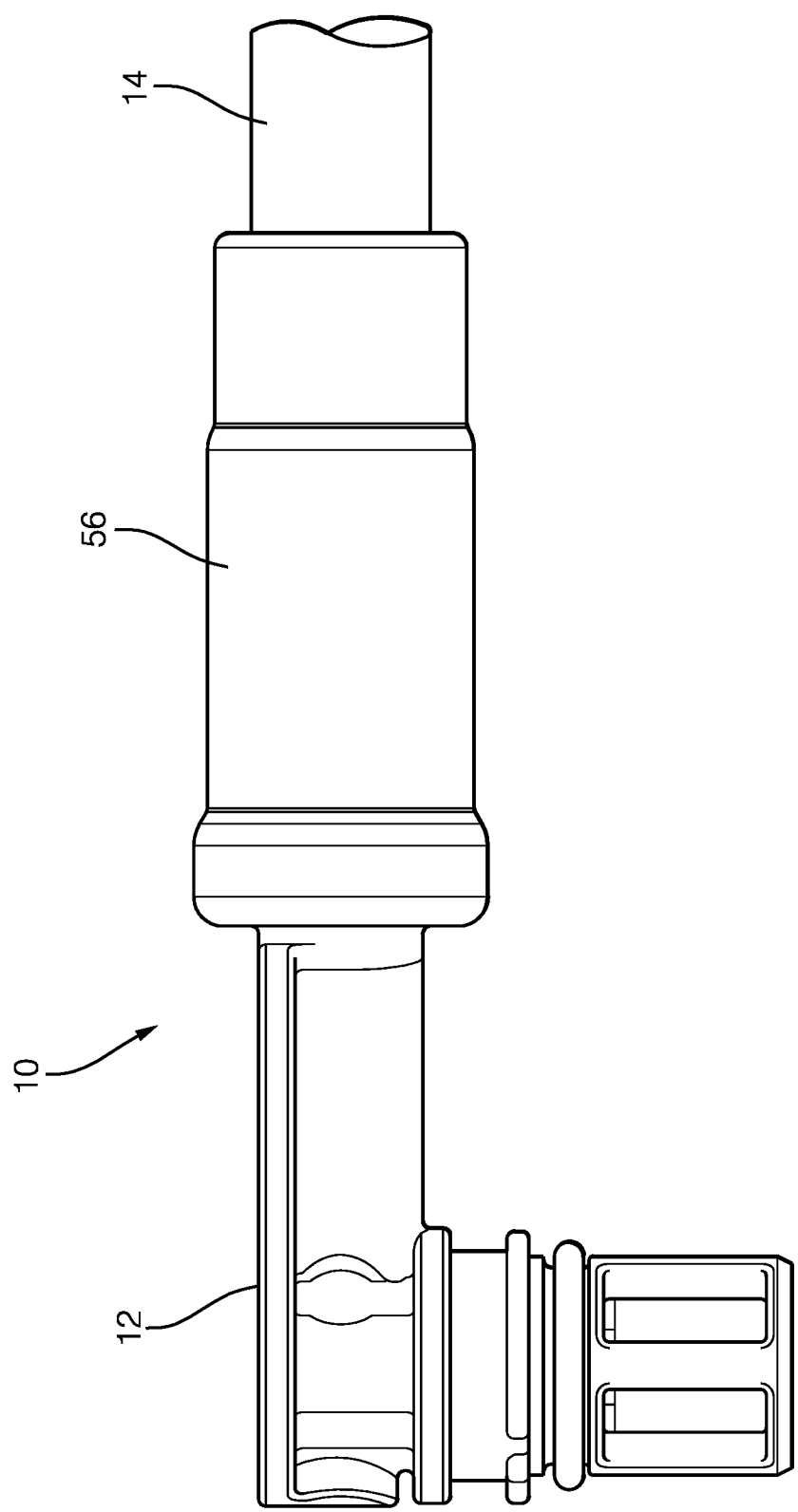
FIG. 9 is a side view of the right angle coaxial terminal of FIG. 2 crimped to the coaxial cable of FIG. 1A with the ferrule enclosed by a sealant according to one embodiment.

As illustrated in FIG. 9, a sealant 58, such as shrink tubing, is placed over the crimping ferrule 56 to inhibit environmental contaminants from entering the internal cavity 28.

Figure 10:
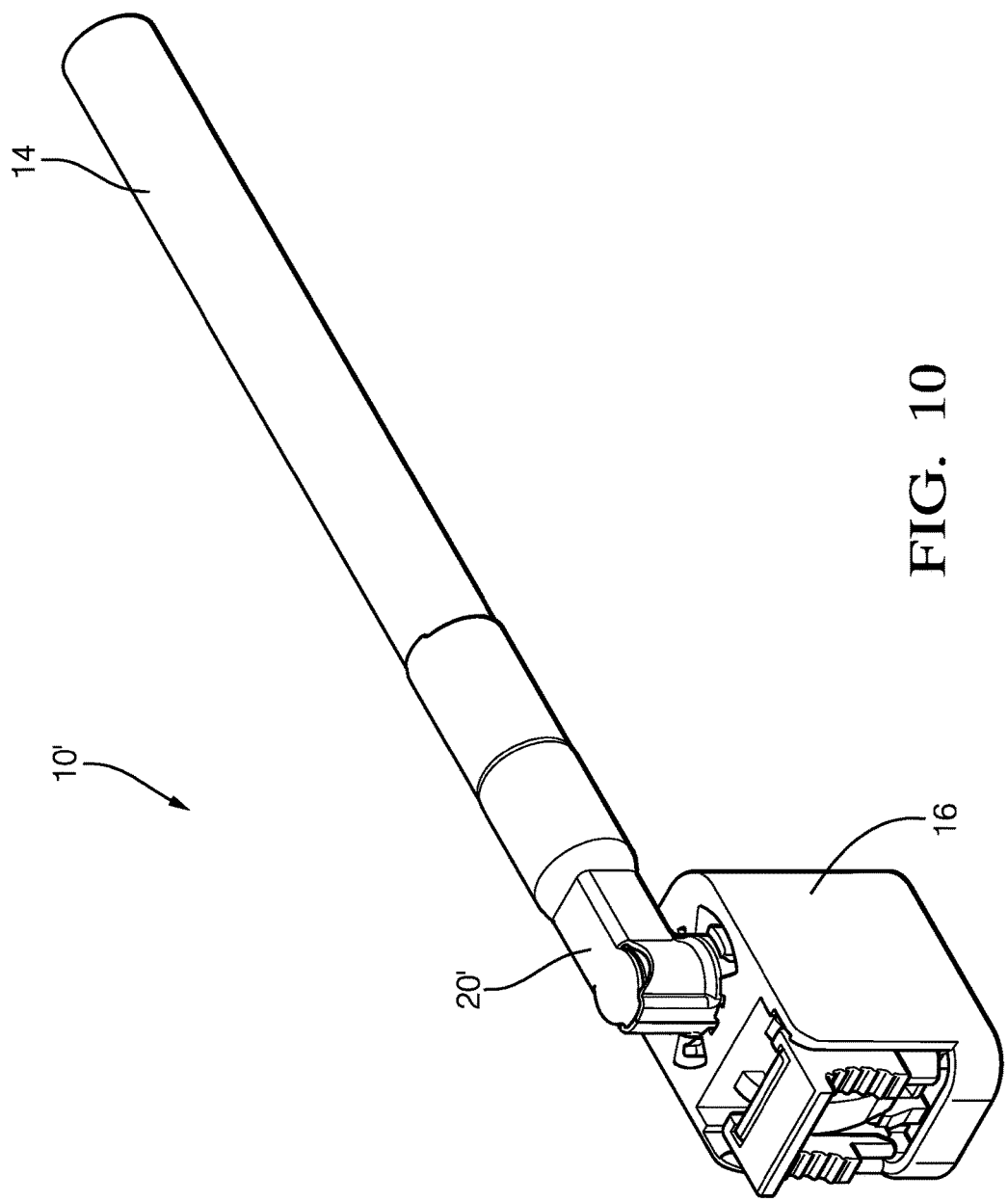
FIG. 10 is a perspective view of a right angle coaxial connector according to a another embodiment.

FIG. 10 illustrates an alternative embodiment of the connector 12'. The inner housing 20' of this connector 12' is formed by bending a stamped piece of sheet metal to form the inner housing 20'. All of the other features of this connector 12 are nearly identical to those of connector 12 described above. This embodiment provides an inner housing 20' that is cheaper to produce than the integral inner housing 20 of connector 12. However, this inner housing 20' does have additional openings that could allow environmental contaminants to enter the internal cavity 28 and so it best suited for applications where this is not a concern.

Figure 11:
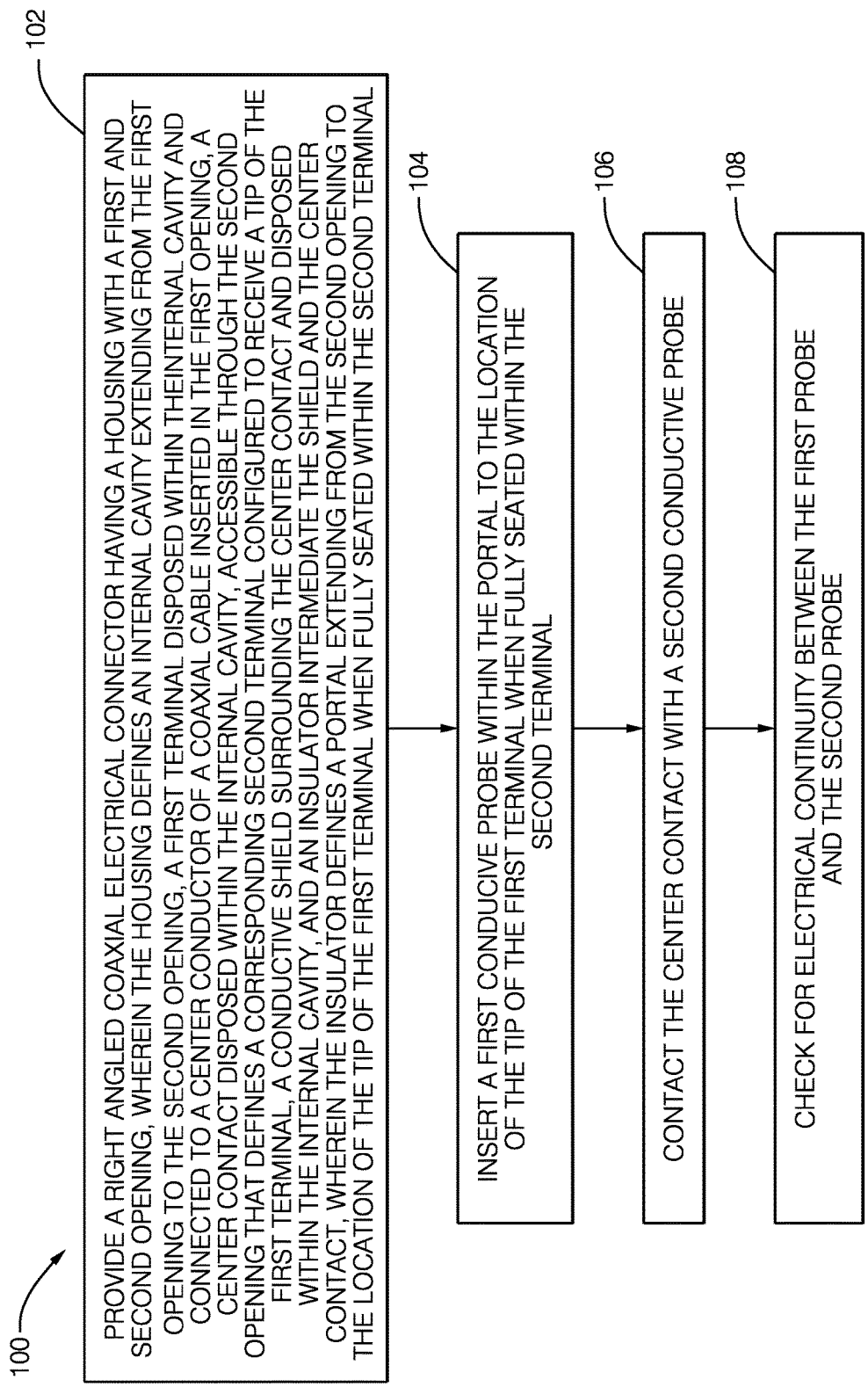
FIG. 11 is a flow chart of a method of electrically verifying proper assembly of a right angled coaxial electrical connector according to yet another embodiment.
Figure 12:
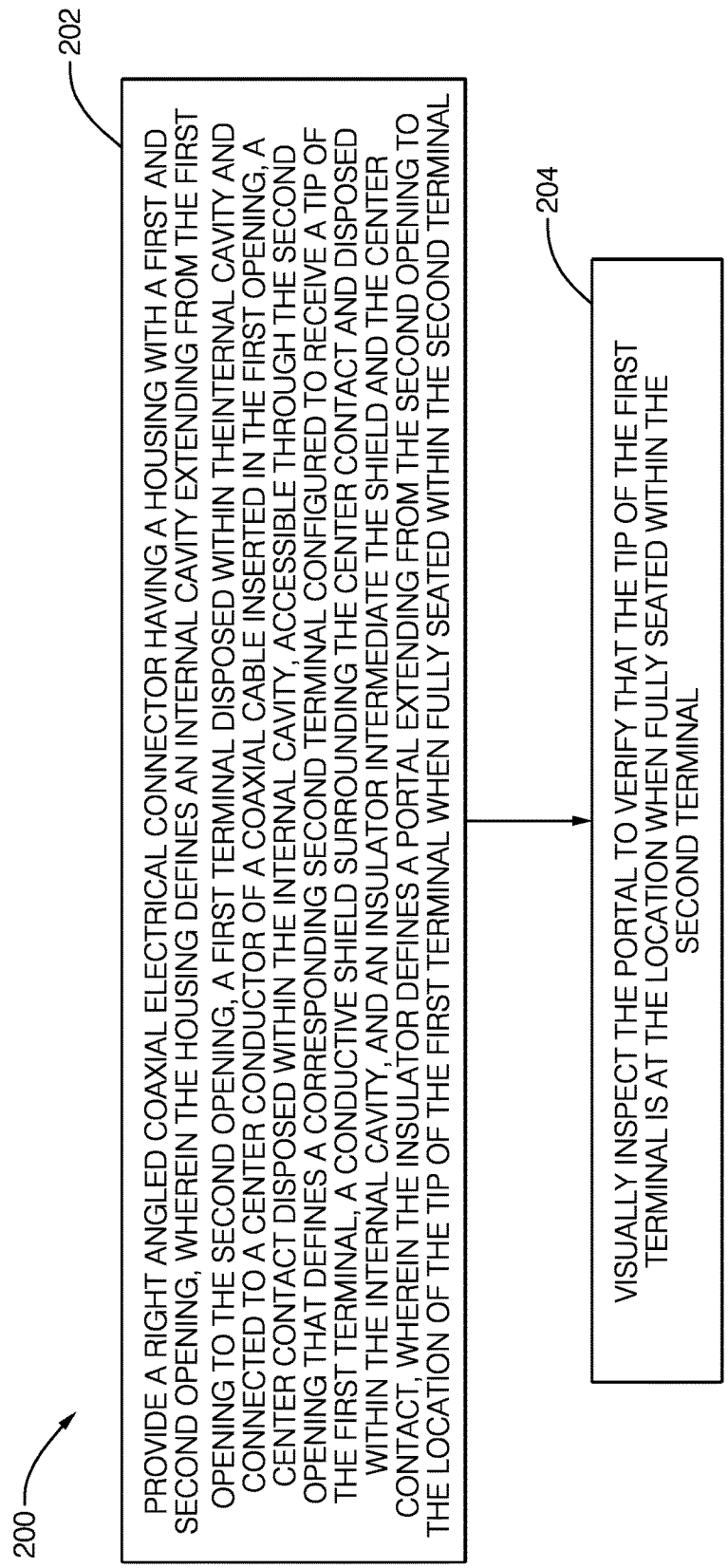
FIG. 12 is a flow chart of a method of visually verifying proper assembly of a right angled coaxial electrical connector according to yet one more embodiment.

A method 100 of verifying proper assembly of a right angled coaxial electrical connector 12 is presented in FIG. 11. The steps of this method 100 are described below:

STEP 102, PROVIDE A RIGHT ANGLED COAXIAL ELECTRICAL CONNECTOR, includes providing a right angled coaxial electrical connector 12 having an inner housing 20 with a first and second opening 22, 24, wherein the inner housing 20 defines an internal cavity 28 extending from the first opening 22 to the second opening 24. A male plug terminal 38 is disposed within the internal cavity 28 and is connected to a center conductor 32 of a coaxial cable 14 inserted in the first opening 22. A center contact 30 is disposed within the internal cavity 28, and is accessible through the second opening 24. The center contact 30 defines a socket terminal that is configured to receive a tip of the male plug terminal 38. A conductive shield surrounding the center contact 30 and is disposed within the internal cavity 28. An insulator 44 is disposed intermediate the shield and the center contact 30. The insulator 44 defines a portal 46 extending from the second opening 24 to the location of the tip of the first terminal when fully seated within the second terminal.

STEP 104, INSERT A FIRST CONDUCIVE PROBE WITHIN THE portal 46, includes inserting a first conducive probe 48 within the portal 46 to the location of the tip of the male plug terminal 38 when fully seated within the socket terminal as shown in FIG. 6.

STEP 106, CONTACT THE CENTER CONTACT WITH A SECOND CONDUCTIVE PROBE, includes contacting the center contact 30 with a second conductive probe 60 as shown in FIG. 6.

STEP 108, CHECK FOR ELECTRICAL CONTINUITY BETWEEN THE FIRST PROBE AND THE SECOND PROBE includes checking for electrical continuity between the first probe 48 and the second probe 60. Electrical continuity between the probes 48, 60 indicates that the plug terminal 38 is indeed received within the female socket terminal 36 of the center contact 30. Electrical continuity between the probes 48, 60 may be checked with a test light, ohmmeter, or any other known device used to check electrical continuity.

Another method 200 of verifying proper assembly of a right angled coaxial electrical connector 12 is presented in FIG. 11. The steps of this method 200 are described below:

STEP 202, PROVIDE A RIGHT ANGLED COAXIAL ELECTRICAL CONNECTOR, includes providing a right angled coaxial electrical connector 12 having a housing with a first and second opening 22, 24, wherein the inner housing 20 defines an internal cavity 28 extending from the first opening 22 to the second opening 24. A male plug terminal 38 is disposed within the internal cavity 28 and is connected to a center conductor 32 of a coaxial cable 14 inserted in the first opening 22. A center contact 30 is disposed within the internal cavity 28, and is accessible through the second opening 24. The center contact 30 defines a socket terminal that is configured to receive a tip of the male plug terminal 38. A conductive shield surrounding the center contact 30 and is disposed within the internal cavity 28. An insulator 44 is disposed intermediate the shield and the center contact 30. The insulator 44 defines a portal 46 extending from the second opening 24 to the location of the tip of the first terminal when fully seated within the second terminal.

Step 204, VISUALLY INSPECT THE PORTAL, includes visually inspecting the portal 46 to verify that the tip of the first terminal is at the location when fully seated within the second terminal as shown in FIGS. 7A and 7B. This visual inspection may be done with a human eye or a machine vision system.

A right angle coaxial connector 12, 12' and methods 100, 200 of verifying proper assembly of the right angled coaxial electrical connector 12, 12' are provided. The connector 12, 12' provides the benefit of checking proper connection of the center conductor 32 of the coaxial cable 14 to the center contact 30 through a portal 46 in the insulator 44 surrounding the center contact 30. This portal 46 eliminates the need for a separate inspection opening to verify proper connection as described in the BACKGROUND OF THE INVENTION section Eliminating the inspection opening simplifies assembly 10 of the connector 12, especially in a sealed connector 12, since the inspection opening does not need to be sealed in a separate manufacturing process. In addition, the connector 12, 12' allows electrical confirmation and/or visual confirmation of the connection of the center conductor 32 to the center contact 30 through the portal 46. Both of these inspection processes may be automated by an automate probing of the portal 46 and center contact 30 or machine vision inspection of the portal 46.

While this invention has been described in terms of the preferred embodiments thereof, it is not intended to be so limited, but rather only to the extent set forth in the claims that follow. Moreover, the use of the terms first, second, etc. does not denote any order of importance, but rather the terms first, second, etc. are used to distinguish one element from another. Furthermore, the use of the terms a, an, etc. do not denote a limitation of quantity, but rather denote the presence of at least one of the referenced items.

We claim:

1. A right angled coaxial electrical connector, comprising:
a housing having a first opening and a second opening, wherein the first opening is oriented at substantially a ninety degree angle to the second opening and wherein the housing defines an internal cavity extending from the first opening to the second opening;
a first terminal disposed within the internal cavity and configured to be connected to a center conductor of a coaxial cable inserted in the first opening;
a center contact disposed within the internal cavity, accessible through the second opening, and defining a corresponding second terminal configured to receive a tip of the first terminal therethrough;
a conductive shield surrounding the center contact and disposed within the internal cavity; and
an insulator intermediate the shield and the center contact, wherein the insulator defines a portal extending generally parallel to the center contact from the second opening to the location of the tip of the first terminal when fully seated within the second terminal.

2. The right angled coaxial electrical connector according to claim 1, wherein the housing does not have a third opening to the internal cavity and did not have a third opening to the internal cavity that is now enclosed by a cover.

3. A method of verifying proper assembly of a right angled coaxial electrical connector, comprising the steps of:
a) providing a right angled coaxial electrical connector comprising:
a housing having a first opening and a second opening, wherein the first opening is oriented at substantially a ninety degree angle to the second opening and wherein the housing defines an internal cavity extending from the first opening to the second opening;
a first terminal disposed within the internal cavity and connected to a center conductor of a coaxial cable inserted in the first opening;
a center contact disposed within the internal cavity, accessible through the second opening, and defining a corresponding second terminal configured to receive a tip of the first terminal therethrough;
a conductive shield surrounding the center contact and disposed within the internal cavity; and
an insulator intermediate the shield and the center contact, wherein the insulator defines a portal extending generally parallel to the center contact from the second opening to the location of the tip of the first terminal when fully seated within the second terminal;
b) inserting a first conducive probe within the portal to the location of the tip of the first terminal when fully seated within the second terminal;
c) contacting the center contact with a second conductive probe; and
d) checking for electrical continuity between the first probe and the second probe.

4. A method of verifying proper assembly of a right angled coaxial electrical connector, comprising the steps of:
a) providing a right angled coaxial electrical connector comprising:
a housing having a first opening and a second opening, wherein the first opening is oriented at substantially a ninety degree angle to the second opening and wherein the housing defines an internal cavity extending from the first opening to the second opening;
a first terminal disposed within the internal cavity and connected to a center conductor of a coaxial cable inserted in the first opening;
a center contact disposed within the internal cavity, accessible through the second opening, and defining a corresponding second terminal configured to receive a tip of the first terminal therethrough;
a conductive shield surrounding the center contact and disposed within the internal cavity; and
an insulator intermediate the shield and the center contact, wherein the insulator defines a portal extending generally parallel to the center contact from the second opening to the location of the tip of the first terminal when fully seated within the second terminal; and
b) visually inspecting the portal to verify that the tip of the first terminal is at the location when fully seated within the second terminal.

5. The method according to claim 4, wherein step b) is performed by a machine vision system.

6. The right angled coaxial electrical connector according to claim 1, wherein the portal is configured to receive a conductive probe to contact the tip of the plug terminal and visually inspect the tip of the plug terminal.

7. The method according to claim 3, wherein the portal is configured to visually inspect the tip of the plug terminal.

8. The method according to claim 4, wherein the portal is configured to receive the first conductive probe.

* * * * *